United States Patent [19]

Kossoff et al.

[11] 4,254,661
[45] Mar. 10, 1981

[54] ULTRASONIC TRANSDUCER ARRAY

[75] Inventors: George Kossoff; David A. Carpenter, both of Northbridge, Australia

[73] Assignee: The Commonwealth of Australia, Phillip, Australia

[21] Appl. No.: 31,528

[22] Filed: Apr. 19, 1979

[30] Foreign Application Priority Data

Apr. 19, 1978 [AU] Australia ............................ 4109/78

[51] Int. Cl.$^3$ .......................................... G01N 29/04
[52] U.S. Cl. ..................................... 73/625; 310/331
[58] Field of Search ................ 73/625, 626, 628, 641; 310/331, 334, 336, 337, 367; 128/660

[56] References Cited

U.S. PATENT DOCUMENTS

| | | | |
|---|---|---|---|
| 2,961,637 | 11/1960 | Camp | 310/337 |
| 3,079,584 | 2/1963 | Sims | 310/337 |
| 3,111,595 | 11/1963 | Junger | 310/367 |
| 3,150,347 | 9/1964 | Hanish | 310/337 |
| 3,699,507 | 10/1972 | Massa | 310/337 |
| 3,982,144 | 9/1976 | Rogers et al. | 310/337 |
| 3,992,693 | 11/1976 | Martin et al. | 310/337 |

FOREIGN PATENT DOCUMENTS

| | | |
|---|---|---|
| 2643126 | 3/1977 | Fed. Rep. of Germany ............. 73/625 |
| 2654280 | 8/1977 | Fed. Rep. of Germany . |
| 1509333 | 5/1978 | United Kingdom . |
| 1517591 | 7/1978 | United Kingdom . |

*Primary Examiner*—Anthony V. Ciarlante

[57] ABSTRACT

Apparatus for the ultrasonic examination of an object, comprises:
a transducer array comprising a plurality of adjacent transducer elements for directing pulses of ultrasonic energy along a beam into the object, characterized in that the width of each of the transducer elements in the direction transverse to the longitudinal direction of the element is non-uniform along the length of the element.

9 Claims, 2 Drawing Figures

ULTRASONIC TRANSDUCER ARRAY

FIELD OF THE INVENTION

This invention relates to the ultrasonic transducers used in ultrasonic echoscopy of objects and in particular to ultrasonic transducer arrays for use at megahertz ultrasonic frequencies in echoscopy techniques designed to produce useful information concerning examined objects (typically, but not exclusively, concerning the more effective acquisition of data in medical diagnosis).

BACKGROUND TO THE INVENTION

Ultrasonic echoscopy provides information about an examined object which may be displayed in the form of an ultrasonic echogram. Such an echogram consists of a display of acoustic impedance discontinuities or reflecting surfaces in the object. It is obtained by directing a short pulse of ultrasonic energy, typically in the 1–30 MHz frequency range, along a line called the beam axis into the examined object where any acoustic impedance discontinuities in the object reflect and return some of the energy along the same beam axis in the form of an echo. This echo is received, converted into an electric signal and displayed as an echogram on a cathode ray oscilloscope, a film, a chart or the like.

The echogram may constitute either a one dimensional or a two dimensional representation and in both cases the information is contained in the position and magnitude of the echo displayed. In a one dimensional display, the position along a base line is used to indicate the distance to the reflecting surface whilst the magnitude of the echo is displayed, for example, as a deflection of the base line or as an intensity change. In a two dimensional display, the position along a base line is used to indicate the distance to the reflecting surface as in a one dimensional display, and the direction of the base line is used to represent the direction of propagation of the acoustic energy which is the beam axis. The two dimensional display is obtained by changing this direction of propagation of the acoustic energy and by instituting a similar but not necessarily identical movement of the base line of the display. The magnitude of the echo is displayed as for a one dimensional display; for example, as a deflection of the base line or as an intensity change.

The technique of ultrasonic echoscopy is used in medical diagnosis to obtain information about the anatomy of patients. The application of this technique is now widely investigated and is described, for example, by D. E. Robinson in "Proceedings of the Institution of Radio and Electronics Engineers Australia," Vol. 31, No. 11, pages 385–392, November, 1970, in his paper entitled: "The Application of Ultrasound in Medical Diagnosis". As pointed out in this article, ultrasonic echoscopy may be used to produce displays resembling anatomical cross-sections which have proved clinically useful when the desired information concerns physical dimensions, shapes of organs or structures or the like. Ultrasonic echography has proved of particular value as a diagnostic aid in the abdomen and pregnant uterus, eye, breast, brain, lung, kidney, liver and heart, these being areas of soft tissue with little bone and air. In general, the technique is considered to complement other techniques to provide a more complete picture of the patients condition, however particularly in pregnancies, ultrasonic echoscopy may be useful in place of X-rays where the latter may not give sufficient information or may be dangerous. In medical use, a pulse of ultrasonic energy is transmitted into a patient in a known direction and echoes are received from reflecting surfaces within the body. The time delay between a transmitted pulse and the received echo depends on the distance from the transmitter to the reflecting surface and the distance information so obtained may be displayed in a suitable way for interpretation and clinical use as a one dimensional range reading or as a two dimensional cross section as previously described.

This known system has suffered from a disadvantage due to the time required to obtain a cross-sectional picture. The cross-sectional picture is made up of a multiplicity of lines of information corresponding to each beam axis position at which a pulse was transmitted and echoes received. The time required to obtain each line of information is fixed by the depth of the tissues of interest and the velocity of propagation of sound in the tissues to be examined. For a particular area of interest neither of these parameters is under the control of the operator and they form a basic limitation on the time required to obtain an echogram.

In U.S. Pat. No. 3,789,833 to Bom, there is disclosed the formation of an array of transducer elements arranged in a line, each providing a separate ultrasonic line of sight. Each array element is pulsed in turn, returned echoes are received and displayed on a screen and then another array element is pulsed. One primed limitation of the system disclosed by Bom is that the line spacing fixes the size of the transducer elements and the resulting ultrasonic resolution. U.S. Pat. No. 3,881,466 to Wilcox discloses the use of a plurality of transducer elements to form each ultrasonic beam, thus breaking the link between line spacing and resolution. In addition, U.S. Pat. No. 3,166,731 to Joy and 3,086,195 to Halliday disclose the application of time delays to signals associated with the various elements of a transducer element array in forming the ultrasonic beam, to cause an electronic steering and focusing action within the plane of scan.

It will thus be apparent that ultrasonic transducers consisting of an array of elements are being used to provide rapid cross sectional imaging, particularly in medical diagnosis. These transducers are usually rectangular piezo-electric ceramic elements sandwiched between two electrodes. The thickness of the element is selected so that the element resonates at the required megahertz ultrasonic frequency (that is, the frequency of the ultrasonic energy to be propagated into the object or medium to be examined). At megahertz frequencies, this means that the thickness of the element is approximately equal to half the wavelength. Imaging is obtained by energising either one or a group of elements to provide a single line of sight of ultrasonic information and a cross sectional image may be built up by sequentially energising the elements as described above. Because of considerations imposed by the number of lines used to form the image and lateral resolution requirements, the width of the elements forming the array typically ranges from the wavelength to two wavelengths, whilst the length dimension of the rectangular elements is usually greater than ten wavelengths.

A common method of constructing such transducer arrays is to use a relatively large rectangular ceramic transducer, corresponding in size to the transducer array, and to divide this transducer to form the individual transducer elements of the array.

One method of construction includes the scribing of fine lines on one or both of the surfaces of the relatively large transducer, to cut through one or both of the electrodes to provide electric insulation between individual elements of the array. This method of array construction results in an array with high sensitivity, for the unenergised transducer material lying alongside an activated array element damps and restrains the transfer of energy from the thickness mode (in which the element is energised) into other modes which could be forced into resonance due to the mechanical coupling that exists within the massive piezo-electric ceramic forming the elements of the array. Unfortunately, the presence of this material allows a small transfer of energy between adjacent elements, which results in a significant cross talk between elements.

In an alternative construction, the relatively massive piezo-electric ceramic transducer is cut through completely to forming form a series of rectangular elements. This method of construction reduces the degree of cross talk between elements since, due to the complete cut, there is no direct mechanical coupling between the adjacent transducer elements. However, as the thickness and the width of the transducer elements are now comparable, there is significant transfer or coupling of energy between adjacent elements due to resonance effects. Consequently, the sensitivity of the element, and thus of the array, is reduced.

SUMMARY OF THE INVENTION

Both cross-talk and loss of sensitivity are overcome by the present invention, which provides a transducer array-typically formed by cutting a relatively large piezo-electric transducer—in which each element of the array is isolated from its neighbor, and width-mode resonance coupling of adjacent elements is eliminated, or at least markedly reduced, by varying the width of the element along its length.

According to the present invention, there is provided, for the megahertz frequency ultrasonic examination of an object, A transducer array comprising a plurality of closely spaced, generally elongate transducer elements arranged for directing pulses of ultrasonic energy into the said object, each element comprising a piezo-electric ceramic material sandwiched between a pair of planar and parallel electrodes characterized in that the width of each of said transducer elements in the direction transverse to its longitudinal direction is non-uniform along the length of the element.

Preferably, the transducer array is a linear transducer array.

In one preferred embodiment of the present invention, the width of each transducer element in the array varies uniformly along the length of the element from one end thereof to the opposite end. In a particularly preferred arrangement of such an array, the plurality of transducer elements comprises a first series of elements in which the width of each element increases uniformly along the length of the element from one end thereof to the opposite end in a given direction, and a second series of transducer elements, the individual elements of which are interposed between the elements of the first series, in which the width of each element decreases constantly along the length of the element from one end thereof to the opposite end in that given direction. In these embodiments of the invention, each of the individual transducer elements of the array may be in the form of a trapezium, with each trapezoidal element being inverted with respect to its immediately adjacent elements.

In further embodiments of the invention, the width of each transducer element may increase and then decrease again, or decrease and then increase again, along the length of the element from one end thereof to the opposite end. In a particularly preferred aspect of this embodiment, the plurality of transducer elements comprises a first series of transducer elements in which the width of each element decreases and then increases again along the length of the element from one end thereof to the opposite end in a given direction, and a second series of transducer elements, the elements of which are interposed between the elements of the first series, in which the width of each element increases and then decreases again along the length of the element from one end thereof to the opposite end in the given direction.

As the transducer elements of the array of this invention are independent, they are preferably mechanically supported by adhesion to a base, for example, a base of an epoxy resin such as "Araldite". Additionally, or alternatively, the individual elements may be bonded by a bonding material between adjacent elements of the array. Such a bonding material may, for example, by an epoxyresin such as "Araldite".

It will be appreciated that the transducer array of the present invention may be used in place of known arrays of rectangular elements in all types of multi-element transducers. In use of the transducer array in apparatus for the megahertz ultrasonic examination of an object, means are provided for energising the elements of the array to direct pulses of ultrasonic energy along a beam into this object. This means may include means for energising the elements of the array in phased relation for focusing and for scanning the beam by sequentially energising the elements of the array. In this manner, control of the time of energising the elements may be used to steer and focus the ultrasonic beam. Further features of the present invention will be apparent from the following description of the embodiments of the invention which are illustrated, in the accompanying drawings.

DETAILED DESCRIPTION OF THE EMBODIMENTS

Figure 1:
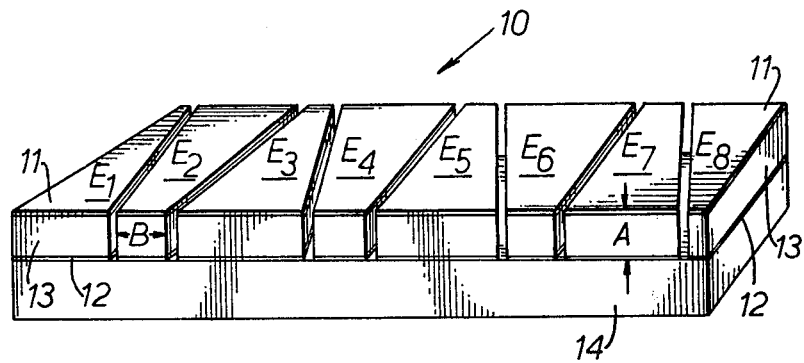
FIG. 1 illustrates, in perspective view, a linear array of trapezoidally shaped ultrasonic transducer elements

Referring firstly to FIG. 1, there is shown a linear array 10 of transducer elements which have been formed from a single piezo-electric ceramic transducer. Each individual transducer element $E_1, E_2, \ldots, E_8$ has the shape of a trapezium. Whilst eight elements are shown as making up the array 10, it will of course be appreciated that the actual number of the elements in an array will be the number required for the apparatus in which the array is to be used. Each of the elements $E_1, E_2, \ldots, E_8$, includes a pair of metal electrodes 11 and 12 which will typically, be of silver or aluminium. The piezo-electric material 13 of the elements is typically barium titanate ceramic. The base 14 of the array, to which each of the elements $E_1$, $E_2$, ..., $E_8$, is bonded to provide mechanical support for the transducer array, may be an epoxy resin.

Figure 3:
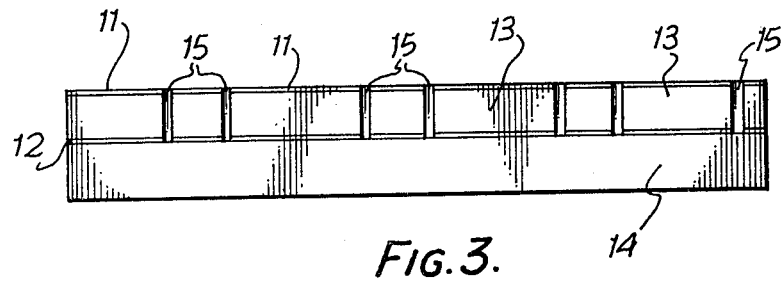
FIG. 3 is a schematic side elevation of a modified form of the array of FIG. 1.

As shown in FIG. 3, the interstitial spaces of the elements of the array may be filled with an acoustically non-coupling material 15. Such a material may be an epoxy resin, for the inclusion of an epoxy resin between individual elements of the array effectively bonds them, for strength, without coupling the elements acoustically.

It will be understood, that if each of the elements $E_1$, $E_2$, ..., $E_8$, is energised simultaneously, an ultrasonic beam at right angles to the free surface of the array will be produced. The beam may, however, be steered electronically by sequentially activating the elements $E_1$, $E_2$, .., $E_8$. Additionally or alternatively, the array 10 may be focused by energising simultaneously the first and last elements ($E_1$ and $E_8$) and then energising the next two elements ($E_2$ and $E_7$) and so on until finally the centre element or elements have been energised. Such means for energising elements of the array are well known in the prior art and for this reason are not shown in the accompanying drawings.

Figure 2:
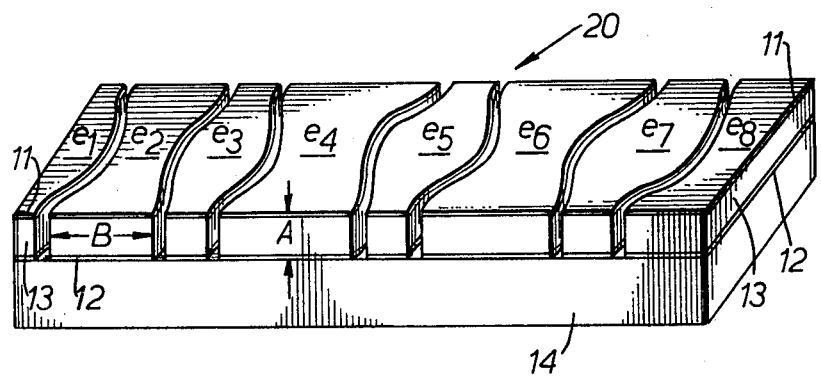
FIG. 2 illustrates, in perspective view, a linear array of ultrasonic elements, each of which has a width which varies non-linearly with its length.

Referring now to FIG. 2 of the drawings, it will be seen that the shapes of the elements $e_1$, $e_2$, ..., $e_8$ thereof differ from the shapes of the elements $E_1$, $E_2$, ..., $E_8$, of FIG. 1. However apart from these different shapes, the array 20 is identical in structure to the array 10 of FIG. 1.

In FIGS. 1 and 2, the letter A is has been used to indicate the thickness resonance mode of each element of the array, whilst the letter B has been used to indicate the width resonance mode of the elements. It has been found that the use of an array of transducer elements, designed to operate at megahertz frequencies, in which each element has a width which varies elements along it length is effective to dampen the width resonance mode of the elements, thus substantially reduce the degree of transfer of energy from the thickness mode of the ultrasonic vibration to width mode of resonance, hence giving high sensitivity for the array. Moreover, the use of a complete cut or separation between the elements of the array eliminates the mechanical coupling between elements and reduces the degree of cross-talk between elements.

It will be appreciated that the particular embodiments referred to above are given by way of exemplification of the present invention only, and many modifications and variations may be made thereto without departing from the spirit and scope of the present invention, as defined in the appended claims.

We claim:

1. A transducer array for use in the megahertz ultrasonic examination of an object, comprising
a plurality of closely spaced, generally elongate transducer elements arranged for directing pulses of ultrasonic energy into the said object, each element comprising a piezo-electric ceramic material sandwiched between a pair of planar and parallel electrodes, characterized in that the width of each of said transducer elements in the direction transverse its longitudinal direction is non-uniform along the length of the element.

2. A transducer array as defined in claim 1, further characterized in that said transducer array is a linear transducer array.

3. A transducer array as defined in claim 1 or claim 2, further characterized in that the width of each transducer element varies uniformly along the length of the element from one end thereof to its other end.

4. A transducer array as defined in claim 1 or claim 2, wherein said plurality of transducer elements comprises a first series of transducer elements in which the width of each element increases uniformly along the length of the element from one end thereof to its other end in a given direction, and a second series of transducer elements, the elements of which are interposed between the elements of said first series, in which the width of each element decreases constantly along the length of the element from one end thereof to its other end in said given direction.

5. A transducer array as claimed in claim 1 or claim 2, wherein said plurality of transducer elements comprises a first series of transducer elements in which the width of each element decreases and then increases again along the length of said element from one end thereof to its other end in a given direction, and a second series of transducer elements, the elements of which are interposed between the elements of said first series, in which the width of each element increases and then decreases again along the length of the said element from one end thereof to its other end in said given direction.

6. A transducer array as defined in claim 1, wherein said plurality of transducer elements are supported on a base.

7. A transducer array as defined in claim 1, further including a bonding material in the spaces between the transducer elements.

8. Apparatus for ultrasonic examination of an object at megahertz frequencies, including a transducer array as defined in claim 1, and means for energising the elements of the said array to direct pulses of ultrasonic energy into the said object.

9. Apparatus as claimed in claim 8, further including means for energising the elements of the said array in phased relation for focusing and scanning said beam.

* * * * *